United States Patent
Redl

(10) Patent No.: US 7,326,412 B2
(45) Date of Patent: Feb. 5, 2008

(54) FIBRINOGEN PLUS A NON-PLASMIN-ACTING FIBRINOLYSIS INHIBITOR FOR THE REDUCTION OR PREVENTION OF ADHESION FORMATION

(75) Inventor: Heinz Redl, Vienna (AT)

(73) Assignees: Baxter International Inc., Deerfield, IL (US); Baxter Healthcare S.A., Zurich (CH)

(*) Notice: Subject to any disclaimer, the term of this patent is extended or adjusted under 35 U.S.C. 154(b) by 318 days.

(21) Appl. No.: 10/399,201

(22) PCT Filed: Oct. 12, 2001

(86) PCT No.: PCT/US01/32043

§ 371 (c)(1),
(2), (4) Date: Jul. 14, 2003

(87) PCT Pub. No.: WO02/30445

PCT Pub. Date: Apr. 18, 2002

(65) Prior Publication Data

US 2004/0043016 A1    Mar. 4, 2004

Related U.S. Application Data

(60) Provisional application No. 60/240,438, filed on Oct. 13, 2000.

(51) Int. Cl.
  *A61K 38/00* (2006.01)
  *A61K 38/48* (2006.01)
(52) U.S. Cl. .................................. 424/94.64; 514/2
(58) Field of Classification Search .................. None
See application file for complete search history.

(56) References Cited

U.S. PATENT DOCUMENTS

| | | | |
|---|---|---|---|
| 4,298,598 A | 11/1981 | Schwarz et al. | |
| 4,359,049 A | 11/1982 | Redl et al. | |
| 4,362,567 A | 12/1982 | Schwarz et al. | |
| 4,377,572 A | 3/1983 | Schwarz et al. | |
| 4,414,976 A | 11/1983 | Schwarz et al. | |
| 4,631,055 A | 12/1986 | Redl et al. | |
| 4,735,616 A | 4/1988 | Eibl et al. | |

FOREIGN PATENT DOCUMENTS

| | | | |
|---|---|---|---|
| EP | 0292472 | 11/1988 | |
| WO | 92/22312 | * 12/1992 | |
| WO | 99/11301 | * 3/1999 | |

OTHER PUBLICATIONS

Donnez et al. Laparoscopic management of large ovarian endometrial cyst: use of fibrin sealant. J. Gynecologic Surg. 7 (3) : 163-6 (1991).*
De Iaco et al., Fibrin sealant in laparoscopic adesion prevention in the rabbit uterine horn model. Fertility and Sterility 62(2) : 400-4 (1994).*
Ono et al., Bone-fibrin mixture in spinal surgery. Clinical Orthopaedics and Related Research 275 : 133-9 (1992).*
Arnold, Peter B., et al. "Evaluation of resorbable barriers for preventing surgical adhesions," Fertility and Sterility, 2000, vol. 73 No. 1, pp. 157-161.
Brands, W., et al. "The Use of Fibrin Glue for Prophylaxis and Therapy of intra-abdominal Adhesions," Der Chirurg, 1990, vol. 61 No. 1, pp. 22-26.
Holmadahl, Lena, et al, "The Role of Fibrinolysis in Adhesion Formation," Eur J Surg, Suppl 1997, Suppl 577, pp. 24-31.
Holmdahl, Lena, et al, "Adhesions: Pathogenesis and Prevention-Panel Discussion and Summary," Eur J Surg, 1997, Suppl 577, pp. 56-62.
Lindenberg, S., et al, "Prevention of Peritoneal Adhesion Formation by Fibrin Sealant *an Experimental Study in Rats*," Annales Chirurgiae et Gynaecologiae, 1984, vol. 73, pp. 11-13.
Takeuchi, M.D., Hiroyuki; et al, "Reduction of Adhesions with Fibrin Glue asfter Laparoscopic Excision of Large Ovarian Endometriomas," The Journal of the American Association of Gynecologic Laparascopists, 1996, vol. 3., No. 4, pp. 575-579.
Toosie, M.D., Katayoun; et al, "Fibrin Glue Reduces Intra-Abdominal Adhesions to Synthetic Mesh in a Rat Ventral Hernia Model," The American Surgeon,2000, vol. 66 No. 1, pp. 41-45.

* cited by examiner

*Primary Examiner*—Sandra E. Saucier
(74) *Attorney, Agent, or Firm*—Townsend and Townsend and Crew LLP

(57) ABSTRACT

Reducing or preventing adhesions which would otherwise form in a patient during or after surgery by administering a fibrinogen preparation containing a non-plasmin-acting fibrinolysis inhibitor such as eglin.

4 Claims, No Drawings

FIBRINOGEN PLUS A NON-PLASMIN-ACTING FIBRINOLYSIS INHIBITOR FOR THE REDUCTION OR PREVENTION OF ADHESION FORMATION

BACKGROUND OF THE INVENTION

Post-surgical adhesions are a major healthcare problem of significant clinical and medical economic relevance. Abdominal adhesions are not only the leading cause of small bowel obstruction but also major sources of infertility and of abdominal and pelvic pain. It could be shown that post-surgical adhesions cause at least 20% of cases of infertility and about 40% of cases of chronic pelvic pain.

The great majority of adhesions in the Western world are induced by surgery. Although it is known that their incidence may be reduced by various improvements in surgical techniques and/or better instrumentation, adhesions cannot be prevented without adjuvant therapy, since every minute trauma may induce their formation.

Therefore, significant efforts have been taken for providing effective means and treatment methods for reducing or preventing adhesions connected with surgery. Many substances or constructs have been reported to have positive effects on surgical adhesions, such as collagen films, collagen gels, sodium hyaluronate/carboxymethylcellulose film and fibrin glue (see e.g. Arnold et al., Fertility and Sterility, 73 (1) (2000), 157-161).

Unfortunately, the process of adhesion and the factors influencing the criticality of such adhesions are largely still unknown. However, it is known that fibrinolysis appears to play a pivotal role in adhesiogenesis (c. Reviews of Holmdal and Holmdal et al. in Eur. J .Surg. (1997); Suppl.577:24-31 and 56-62 incorporated herein by reference).

The effect of the application of fibrinogen preparations or fibrin glues on anti-adhesion is highly controversial. Many earlier reports claim the possibility of prevention of the formation of postsurgical adhesions with such fibrin glues (e.g. Brands et al., Chirurg 61 (1990): 22-26; Lindenberg et al., Ann. Chir. Gynecol. 73 (1984): 11-13; De laco et al., Fertility and Sterility 62 (2) (94): 400-404 and Takeuchi et al. (J. Am. Assoc. Gynecol. Laparosc. 3 (4) (1996): 575-579) or fibrinogen preparations, such as human cryoprecipiate (Toosie et al., The American Surgeon 66 (2000): 41-45).

However, other reports detected no significant effect in preventing adhesion formation or reproductive outcome after adhesion complications during surgery (see e.g. Marana et al., Gynecol. Obstet. lnvest. 41 (1996): 199-202 and Gauwerky et al., Arch. Gynecol. Obstet. 247 (1990): 161-166).

Recent research has concentrated on the development of barriers of fibrinolytic drugs and of selected agents, such as phospholipids. Comparative tests showed that resorbable barriers, such as collagen gels, collagen films and sodium hyaluronate/carboxymethylcellulose films, were effective in significantly reducing adhesion formation, whereas use of fibrin glues led to an incidence of adhesion formation similar to that in untreated control animals (see Arnold et al.; Holmdal (see supra)). These authors also demonstrated that the types of fibrinolytic inhibitors contained in all commercially available fibrin sealants significantly increased adhesion formation both to the parietal peritoneum and to the bowel compared with untreated control animals, whereas fibrinolytic activation with a recombinant tissue type plasminogen activator eliminated adhesion formation to the injured bowel and significantly reduced the number and extent of adhesions in the parietal peritoneum compared with untreated control animals.

It is therefore an object of the present invention to provide for a method for efficiently reducing or preventing adhesion in a patient as well as for the use of specific fibrinogen preparations for adhesion reduction or prevention.

SUMMARY OF THE INVENTION

The invention provides a method for reducing or preventing adhesions which would form in a patient during or after surgery, said method comprising administering to said patient an effective amount of a fibrinogen preparation containing a non-plasmin acting fibrinolysis inhibitor. The invention also provides the use of a non-plasmin acting fibrinolysis inhibitor in the preparation of a fibrinogen preparation for the reduction or prevention of post-surgical adhesions.

Although recent reports indicated that fibrinogen preparations, such as fibrin sealants, have no significant effect for preventing or reducing adhesions, it was shown by the present inventors that the use of direct plasmin-acting fibrinolysis inhibitors in fibrinogen preparations have negative effects on the performance of such fibrinogen preparations in adhesion prevention. Since direct plasmin-acting fibrinolysis inhibitors, such as aprotinin, are contained in almost all commecially available tissue adhesives, it may be that the lack of performance of fibrinogen preparations for preventing adhesions, as described in recent publications (Holmdal, supra; Arnold et al, supra), is related to the presence of such direct plasmin-acting fibrinolysis inhibitors. Surprisingly, it was discovered that post-surgical adhesions are reduced or prevented when fibrinogen preparations are used with fibrinolysis inhibitors which act mainly via a non-plasmin pathway.

DETAILED DESCRIPTION OF THE INVENTION

The method according to the present invention is efficient in reducing or preventing adhesions in a patient by administering a fibrinogen preparation which contains a non-plasmin acting fibrinolysis inhibitor. The presence of a fibrinolysis inhibitor is preferred in such fibrinogen preparations in order to delay endogenous lysis of the fibrin clot which is formed at the wound site upon reaction of fibrinogen with thrombin. Thrombin can be provided in a kit together with the fibrinogen preparation and is then added exogeneously to the fibrinogen preparation. Alternatively, the fibrinogen preparation reacts with thrombin which is endogeneously present at the wound site. The adhesions to be reduced or prevented with the method according to the present invention are those described in the prior art and may be adhesions to or between organs, parts of organs or tissues in a particular location. Generally adhesions may be defined as abnormal attachments between tissues and organs. Such attachments may be developed in response to trauma to the peritoneum. There trauma may be inflammatory or surgical and may include: exposure to infection or to intestinal contents, ischemia, initation from exogeneous materials (such as sutures, gauze particles or glove dusting powder), abrasion, desiccation or overheating by lamps or irrigation fluids.

The most relevant clinical adhesions are described as malformations or fibrinaceous glueings of peritoneum covered entrails which may lead to adhesion or briden ileus.

More specifically, such adhesions may occur after injury to or deformation of the peritoneum during surgery which may be caused e.g. by abdominal surgery, reproductive surgery, spinal surgery, laparatomy or other surgery in cardiac or abdominal procedure or in the gynecological area.

The patient may be human or any animal having or having a risk for such adhesions. Especially adhesions involving key agens and tissues, e.g. the small intestine or the uterus and adnexa, which are the most likely to be symptomatic, are preferably treated or prevented.

A "non-plasmin-acting" fibrinolysis inhibitor is an inhibitor with a fibrinolysis inhibiting activity which activity is mainly based on a non-plasmin mechanism. Examples for such inhibitors are the elastase inhibitors as described in the WO 99/11301, incorporated herein by reference.

Another group of preferred "non-plasmin acting" fibrinolysis inhibitors according to the present invention are those inhibitors which act mainly on plasminogen and therefore do also belong to the group of non-plasmin acting fibrinolysis inhibitors, because through their action, plasmin is not formed from plasminogen. Examples for those types of inhibitors are tranexamic acid and epsilon-amino-caproic acid.

On the other hand, "plasmin-acting" fibrinolysis inhibitors are inhibitors which prevent the fibrinolysis process mainly by inhibiting plasmin directly. This group of inhibitors includes substances like aprotinin.

According to the present invention the non-plasmin-acting fibrinolysis inhibitor preferably is an elastase inhibitor. Such preferred elastase inhibitors are selected from the group consisting of eglin, alpha1-proteinase inhibitor (=alpha-1-antiprotease), leukocyte protease inhibitor, elafin, alpha-2 macroglobulin and mixtures thereof.

When used in combination with fibrinogen, fibrinolysis inhibitors which do not mainly act directly on plasmin can efficiently reduce or prevent adhesions with would otherwise form in a patient during or after surgery. In contrast to fibrinogen preparations without anti-fibrinolytic activity, the use of the non-plasmin-acting inhibitors allows a controlled lytic process in the clot formed in vivo, which leads to an efficient healing process. The usefulness of non-plasmin-acting fibrinolysis inhibitors for controlled clot lysis, particularly in tissues with increased fibrinolytic activity, was disclosed in WO 99/11301.

In the method according to the present invention it is preferred to apply a thrombin preparation simultaneously with the fibrinogen preparation as known from the "classical" fibrinogen based tissue adhesives, as disclosed e.g. in the U.S. Pat. Nos. 4,298,598; 4,362,567; 4,377,572 and 4,414,976 as well as in all the patents or applications citing these patents or their corresponding counterparts in other countries, which are incorporated herein by reference.

The thrombin preparation and the fibrinogen preparation may be provided as a set, preferably together with suitable administration devices which are described in the EP 0 037 393 A, EP 0 315 222 A, EP 0 156 098 A, EP 0 210 160 A and EP 0 292 472 A, which are incorporated herein by reference.

The adhesions which are to be reduced or prevented would result from abdominal surgery, gynecological reproductive surgery, spinal and laparoscopic surgery. These adhesions would be those which would newly form or those which would reform after adhesiolysis, if the present invention were not used.

The fibrinogen preparation is preferably provided as a tissue adhesive preparation and therefore contains all ingredients and concentrations which are known to be preferred in such tissue adhesives. Especially the presence of factor XIII in suitable amounts is preferred. Other substances which may be present may be antibiotics, cytokines, etc. Plasmin-acting fibrinolysis inhibitors should not be used with the present invention. The recent results of Toosie et al. (see supra), wherein human cryoprecipitate, without a plasmin-acting inhibitor, has been applied, show that such a cryoprecipitate without any fibrinolysis inhibitor reduces intra-abdominal adhesions.

An "effective amount" of a fibrinogen preparation according to the present invention is any amount which is able to reduce or prevent adhesion formation in a patient significantly as compared to a control group without such an administration. Examples for such amounts are fibrinogen concentrations between 30 and 80 mg/ml, preferably around 40 mg/ml.

According to a further aspect, the present invention relates to the use of a fibrinogen preparation containing a non-plasmin-acting fibrinolysis inhibitor for producing a preparation for reduction or prevention of adhesion formation in a patient during or after surgery.

Yet another aspect relates to a preparation for reducing or preventing adhesion formation in a patient during or after surgery which preparation comprises fibrinogen and a non-plasmin-acting fibrinolysis inhibitor or a set comprising a component A containing a fibrinogen component as disclosed in the present application and a component B comprising a thrombin preparation.

The invention will now be explained in more detail by way of the following examples to which, however, it shall not be restricted.

EXAMPLES

1. Reduction and Prevention of Adhesion Using an Eglin Containing Fibrinogen Preparation For the present test a fibrinogen containing preparation (40 mg/ml fibrinogen; 1-3 U/ml Factor XIII) was mixed with eglin as a non-plasminogen-pathway fibrinolysis inhibitor to achieve a final concentration of 1 mg eglin per ml.

A modified rabbit model according to Rogers et al. (J. Invest. Surg.9 (1996), 385-391 and J. Invest. Surg.10 (1997), 31-36) was used for testing abdominal adhesion prevention involving formation of a peritoneal lesion and an additional defect in the cecum.

Rabbits are anesthetized and a median laparatomy is performed. The cecum is exposed and the upper side gently abraded with a gauze swab to induce de-epithelialization of the serosal surface of an approximately 30 $cm^2$ area until petechial bleeding occurs in the absence of muscle damage. Thereafter dynamic digital pressure is exerted to create subserosal hemorrhages over the surface of the cecum. In addition the lateral abdominal wall associated with the cecum position is pressed through a fixation frame causing protrusion of a 4.5×3 cm area of the parietal peritoneum. The externalized parietal wall is traumatized by removal of the peritoneum and the underlying transversal abdominal musculature.

To both lesions, test or control solutions in their predetermined volume are applied and the test solution is left to clot for 5 min. The distance of the delivery device from the surface of the tissue is around 10 cm. After 5 min both in the test group and control group the surface is wetted with 5 ml saline to prevent the area from drying up. The abdomen is closed. The muscle and skin incisions are sutured separately using Synthofil☐ 2/0 or Steelex 0/4 as interrupted sutures in a three-level manner.

For a period of 14 days, the animals are monitored daily for weight and clinical condition. At day 14 the animals are sacrificed and necropsies are performed to determine and quantify adhesion formation on the abdominal wall.

The adhesions are quantified by calibrated calipers. The area of attachment to the abdominal wall is calculated in $mm^2$ by multiplying the length and width of the adhesion attachment.

The results of the present tests are depicted in the following table 1.

TABLE 1

| Animal No. | Treatment | Surface area of Adhesion ($mm^2$) |
|---|---|---|
| 1 | fg + eglin | 0 |
| 2 | fg + eglin | 0 |
| 3 | fg + eglin | 0 |
| 4 | fg + eglin | 0 |
| 5 | fg + eglin | 0 |
| 6 | fg + eglin | 0 |
| 7 | no fg | 1248 |
| 8 | no fg | 1482 |
| 9 | no fg | 0 |
| 10 | no fg | 1960 |
| 11 | no fg | 2200 |
| 12 | no fg | 1677 |
| 13 | no fg | 0 |
| 14 | no fg | 100 |
| 15 | no fg | 550 |
| 16 | no fg | 1900 | fg + eglin = fibrinogen + eglin
no fg = control animals not treated with fibrinogen solution No adhesions have been observed with animals treated with eglin containing fibrinogen solution, whereas for the untreated control animals median surface area which was effected by adhesion was 1365 $mm^2$.

2. Comparative Example: Treatment with Aprotinin Containing Fibrinogen Solution

According to the "Closure" model, the caecum was abraded with a gauze until petechial bleeding occurred. This lesion was exposed to the air to induce drying. In addition, a defect of peritoneum underlying the right abdominal wall together with the attached muscle was performed which was sutured subsequently. The caecum and the peritoneal lesion were sprayed with the composition to be tested using a spray device or untreated as a control, then left five minutes to clot before wound closure.

Results with the 3 different preparations, Tisseel with added aprotinin, Tisseel without aprotinin and Sealagen, as well as the control are shown in Table 2.

TABLE 2

| "Tisseel" preparation with aprotinin | | "Tisseel" preparation without aprotinin | | "Sealagen" preparation (no inhibitor) | | Control | |
|---|---|---|---|---|---|---|---|
| Prot. No. | $mm^2$ | Prot. No. | $mm^2$ | Prot. No. | $mm^2$ | Prot. No. | $mm^2$ |
| 9 | 7.0 | 51 | 5.5 | 6 | 3.0 | 3 | 14.0 |
| 12 | 2.0 | 52 | 8.0 | 8 | 1.0 | 4 | 9.0 |
| 21 | 4.0 | 53 | 19.5 | 18 | 0.0 | 14 | 8.0 |
| 22 | 3.0 | 54 | 5.0 | 20 | 3.0 | 16 | 104.0 |
| 49 | 103.0 | 55 | 23.5 | 29 | 0.0 | 47 | 13.0 |
| 50 | 58.0 | 56 | 0.0 | 31 | 0.0 | 48 | 13.0 |
| 67 | 11.0 | 81 | 0.0 | 105 | 14.0 | 63 | 78.0 |
| 68 | 14.0 | 82 | 5.0 | 120 | 15.0 | 64 | 12.5 |
| 71 | 8.0 | 91 | 0.3 | 119 | 0.0 | 69 | 18.0 |
| 72 | 7.5 | 92 | 0.0 | 108 | 0.0 | 70 | 8.0 |
| 77 | 55.0 | 95 | 12.0 | 109 | 0.0 | 75 | 20.0 |
| 78 | 20.0 | 96 | 21.0 | 110 | 0.0 | 76 | 116.0 |
| Mean | 24 | Mean | 8 | Mean | 3 | Mean | 34 |
| SD | 30 | SD | 8 | SD | 5 | SD | 38 |
| SEM | 9 | SEM | 2 | SEM | 2 | SEM | 11 |
| median | 10 | median | 5 | median | 0 | median | 14 |

I claim:

1. A method for reducing or preventing adhesion formation in a subject after gynecological or reproductive surgery comprising administering to said subject a fibrinogen preparation containing a non-plasmin-acting fibrinolysis inhibitor, wherein said non-plasmin-acting fibrinolysis inhibitor is eglin in an amount of 1 mg/ml in the fibrinogen preparation, in an amount effective to reduce or prevent adhesions.

2. A method according to claim 1 wherein a thrombin preparation is administered simultaneously with said fibrinogen preparation.

3. A method according to claim 1 wherein said surgery is laparoscopic surgery.

4. A method according to claim 1 wherein said fibrinogen preparation contains factor XIII.

* * * * *